US00PP09973P

United States Patent [19]

Meilland

[11] Patent Number: Plant 9,973

[45] Date of Patent: Jul. 22, 1997

[54] MINIATURE ROSE PLANT NAMED 'MEIKANROU'

[75] Inventor: Alain A. Meilland, Antibes, France

[73] Assignee: The Conard-Pyle Company, West Grove, Pa.

[21] Appl. No.: 654,260

[22] Filed: May 28, 1996

[51] Int. Cl.[6] ..... A01H 5/00

[52] U.S. Cl. ..... Plt./10

[58] Field of Search ..... Plt./10

*Primary Examiner*—Howard J. Locker

*Attorney, Agent, or Firm*—Burns, Doane, Swecker & Mathis, L.L.P.

[57] ABSTRACT

A new and distinct variety of rose plant of the Miniature Class is provided which abundantly forms attractive dark red blossoms that are highly stable with respect to coloration. The plant is bushy, and forms dense medium-green semi-glossy vegetation. The blossoms possess no fragrance. The plant is well adapted to pot forcing under greenhouse growing conditions, and grows well on its own roots. An excellent ovoid commercial bud form is exhibited. The plant is particularly well-suited for use as attractive ornamentation in the landscape.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the 'Mogral' variety (non-patented in the United States). The male parent (i.e., the pollen parent) of the new variety was the product of the pollination of the 'Meichanso' variety (non-patented in the United States) and the 'Ruiredro' variety U.S. Plant Pat. No. 5,976). The 'Meichanso' variety sometimes is known as the 'Parador' variety. The parentage of the new variety can be summarized as follows:

'Mogral'×('Meichanso'×'Ruiredro').

The seeds resulting from the above pollination were sown and 34 small plants were obtained which were physically and biologically different from each other. Selective study resulted in the identification of a single plant of the new variety.

It was found that the new variety of Miniature rose plant of the present invention possesses the following combination of characteristics:

(a) forms in abundance attractive dark red blossoms that are very stable in coloration,
(b) forms medium-green semi-glossy foliage,
(c) exhibits a bushy growth habit,
(d) is well adapted to pot forcing under greenhouse growing conditions, and
(e) grows well on its own roots.

The coloration stability of the dark red blossoms is particularly noteworthy. Also, an excellent ovoid commercial bud form is exhibited The new variety well meets the needs of the horticultural industry. It is particularly well-suited for use as attractive ornamentation in the landscape.

The new variety has been found to undergo asexual propagation in France by a number of routes, including budding, grafting, cuttage, etc. Asexual propagation by the above-mentioned methods as performed in France has shown that the characteristics of the new variety are strictly transmissible from one generation to another.

The new variety has been named the 'Meikanrou' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were observed during November while growing on their own roots in greenhouses at Le Cannet des Maures, Var, France.

DETAILED DESCRIPTION

Figures 1, 2, 3, 4, 5, 6, 7, 8, 9, 10, 11, 12, 13, 14, 15, 16:
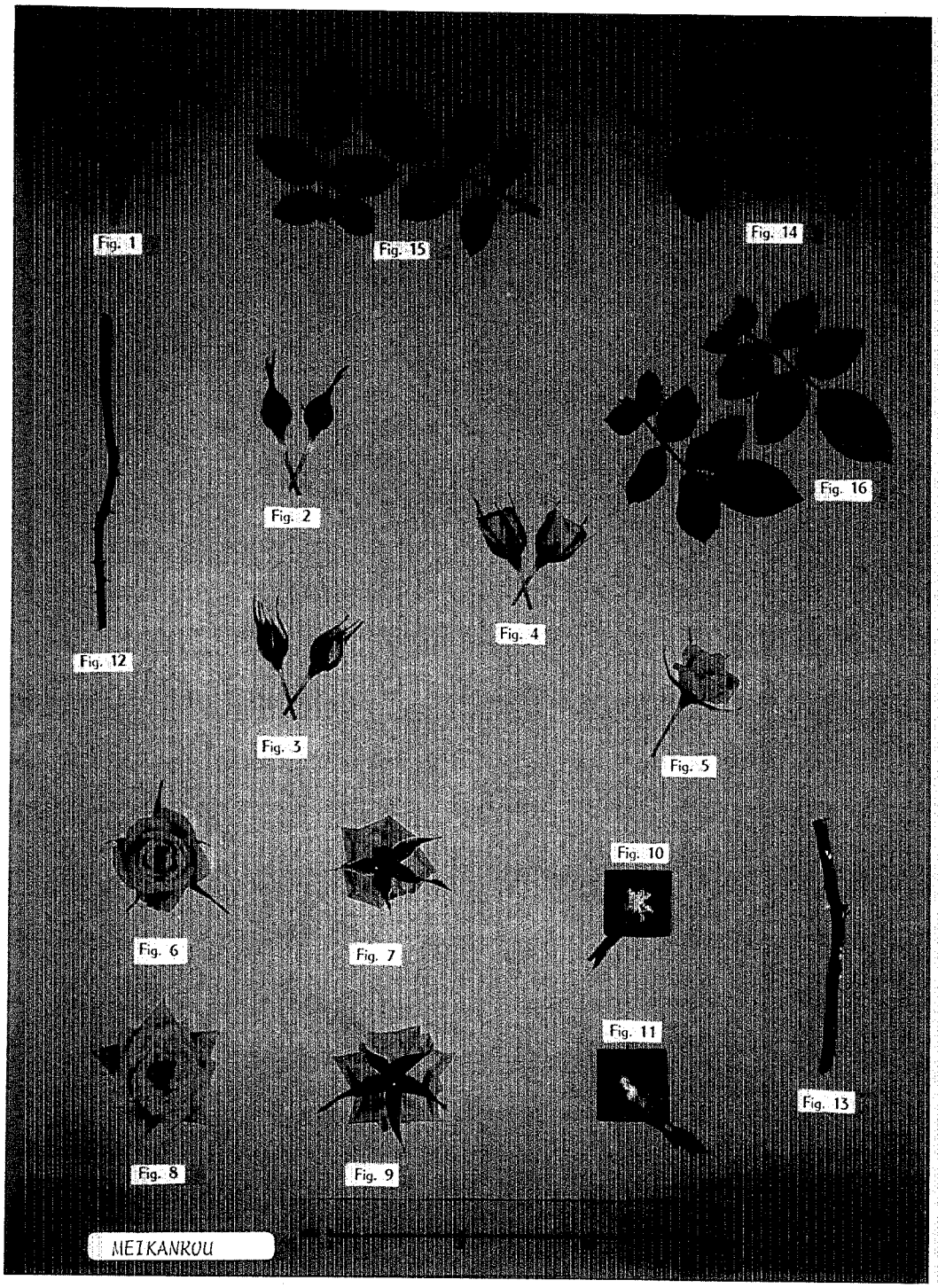
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates specimens of two floral buds at the opening of the petals.
FIG. 5 illustrates a specimen of a flower during the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown at the right and the under surface being shown at the left.
FIG. 15 illustrates specimens of leaves with five leaflets with the upper surface being shown at the right and the under surface being shown at the left.
FIG. 16 illustrates specimens of leaves with seven leaflets with the upper surface being shown at the bottom left and the under surface being shown at the top right.

The chart used in the identification of the colors is that of The Royal Horticultural Society (R.H.S. Colour Chart). The terminology which precedes reference to the chart has been added to indicate the corresponding colors in more common terms. The description is based on two year-old specimens of the new variety which were observed during November while growing on their own roots in greenhouses at LeCannet des Maures, Var, France.

Class: Miniature.

Plant:

*Height.*—Approximately 25 cm. on average at the end of the growing season.

*Habit.*—Bushy.

Branches:

*Color.*—Young stems: Grass Green, Green Group 143B. Adult wood: medium green, Green Group 137C.

*Thorns.*—Size: small. Quantity: moderately numerous. Color: reddish in coloration on young stems and havana brown on adult stems.

Leaves:

*Petioles.*—Upper surface: striped, reddish on young foliage and medium green on mature foliage with more or less glandular edges. Under surface: light green and rarely with some small thorns.

*Stipules.*—Adnate, pectinate, wide and linear.

*Leaflets.*—Number: 3, 5, and 7. Shape: elliptic. Serration: simple and regular (as illustrated). Texture: normal or typical for this class. General appearance: dense and semi-glossy medium green foliage. Color: (young foliage): Upper surface: medium green, Green Group 137B. Under surface: light green, Green Group 137C. Color (adult foliage): Upper surface: dark green, Green Group 137A. Under surface: medium green, Green Group 137C.

Inflorescence:

*Number of flowers.*—Approximately 1 and 4 per stem.

*Peduncle.*—Medium green, smooth, and its length is approximately 2 to 3 cm. on average.

*Sepals.*—Upper surface: tomentose and greenish in coloration. Under surface: medium green with few extensions (as illustrated).

*Buds.*—Shape: excellent ovoid commercial bud form. Length: approximately 1.5 to 2 cm. on average. Size: medium for this class. Color upon opening: Upper surface: Currant Red, Red Group 46A. Under surface: near Cardinal Red, Red Group 53B.

*Flower.*—Form: cupped. Diameter: approximately 5.5 cm. on average. Color (when opening begins): Upper surface: near Currant Red, Red Group 46A. Under surface: near Cardinal Red, Red Group 53B. Color (when blooming): Upper surface: near Currant Red, Red Group 46A. Under surface: near Cardinal Red, Red Group 53B. Color (at end of blooming): Upper surface: near Currant Red, Red Group 46A. Under surface: near Cardinal Red, Red Group 53B. Fragrance: none. Lasting quality: very long when on the plant. Petal number: approximately 65 to 85 on average. Petal form: the outer petals are rounded with reflexed edges and the inner petals are oval. Petal drop: good. Anthers: normal and ochure in coloration. Stamen number: approximately 32 on average. Filaments: bright yellow in coloration. Pistil number: approximately 18 to 25 on average. Stigmas: normal, and strawlike in coloration. Styles: greenish in coloration. Receptacle: medium green, smooth, and in longitudinal section in the shape of a pitcher.

Development:

*Vegetation.*—Dense.

*Blooming.*—Abundant.

*Aptitude to bear fruit.*—Poor.

*Resistance to diseases.*—Good.

I claim:

1. A new and distinct variety of Miniature rose plant characterized by the following combination of characteristics:

(a) forms in abundance attractive dark red blossoms that are very stable in coloration,
(b) forms medium-green semi-glossy foliage,
(c) exhibits a bushy growth habit,
(d) is well adapted to pot forcing under greenhouse growing conditions, and
(e) grows well on its own roots;

substantially as herein shown and described.

* * * * *

MEIKANKOU